(12) United States Patent
de Smet

(10) Patent No.: US 8,395,380 B2
(45) Date of Patent: Mar. 12, 2013

(54) DEVICE FOR NON-DESTRUCTIVE TESTING OF A COMPONENT BY ANALYZING DISTRIBUTION OF A LEAKAGE MAGNETIC FIELD

(75) Inventor: Marie-Anne de Smet, Monbrun (FR)

(73) Assignee: Airbus Operations SAS, Toulouse (FR)

( * ) Notice: Subject to any disclaimer, the term of this patent is extended or adjusted under 35 U.S.C. 154(b) by 920 days.

(21) Appl. No.: 12/301,701

(22) PCT Filed: May 16, 2007

(86) PCT No.: PCT/EP2007/054751
§ 371 (c)(1),
(2), (4) Date: Jun. 23, 2009

(87) PCT Pub. No.: WO2007/135051
PCT Pub. Date: Nov. 29, 2007

(65) Prior Publication Data
US 2009/0302836 A1    Dec. 10, 2009

(30) Foreign Application Priority Data

May 24, 2006   (FR) ...................................... 06 51901

(51) Int. Cl.
*G01R 33/02*   (2006.01)
*G01N 27/82*   (2006.01)

(52) U.S. Cl. ..................... 324/244.1; 324/234; 324/240; 324/243; 324/262

(58) Field of Classification Search .................. 324/240, 324/244.1, 234, 262, 243
See application file for complete search history.

(56) References Cited

U.S. PATENT DOCUMENTS

| | | |
|---|---|---|
| 3,511,086 A | 5/1970 | Woodmansee |
| 3,970,074 A | 7/1976 | Mogos et al. |
| 4,433,637 A | 2/1984 | Buirley et al. |
| 5,047,719 A | 9/1991 | Johnson et al. |
| 5,659,248 A | 8/1997 | Hedengren et al. |
| 6,077,228 A | 6/2000 | Schonberger |
| 2001/0015643 A1 | 8/2001 | Goldfine et al. |
| 2003/0031296 A1 | 2/2003 | Hoheisel |
| 2005/0062470 A1 | 3/2005 | Shoji |

FOREIGN PATENT DOCUMENTS

| | | |
|---|---|---|
| DE | 4220544 A1 | 1/1994 |
| EP | 0245147 A | 11/1987 |
| EP | 0577244 A2 | 1/1994 |
| EP | 0672380 A | 9/1995 |
| EP | 0887642 A1 | 12/1998 |
| FR | 2436994 A1 | 9/2003 |
| FR | 1403635 A | 3/2004 |

OTHER PUBLICATIONS

International Search Report dated Aug. 14, 2007, PCT/EP2007/054751.

*Primary Examiner* — Reena Aurora

(74) *Attorney, Agent, or Firm* — Perman & Green, LLP

(57) ABSTRACT

A device for non-destructive control of a component analyzes distribution of a leakage magnetic field emitted by the component when it is subjected to an exciting magnetic field, includes means for generating an exciting magnetic field inside the component to be tested, and means for detecting and measuring the distribution of the magnetic field. The set of means is integrated in a flexible housing to form a device in the form of a flexible coating for being fixed on a region of the surface of the component to be tested. The disclosed embodiments are useful for non-destructive testing of aircraft components, but may also be used in all industrial sectors where testing the integrity of components is important, such as the automotive, railway, marine or nuclear industry.

26 Claims, 3 Drawing Sheets

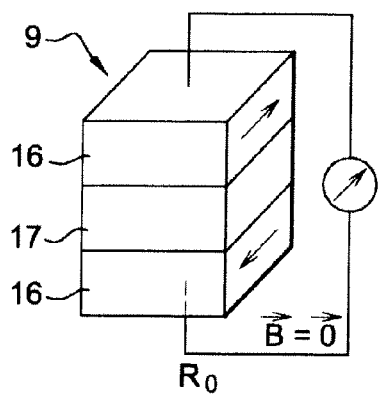
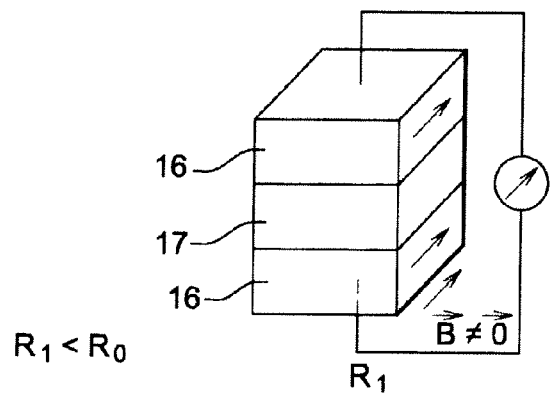
Fig. 4A     Fig. 4B
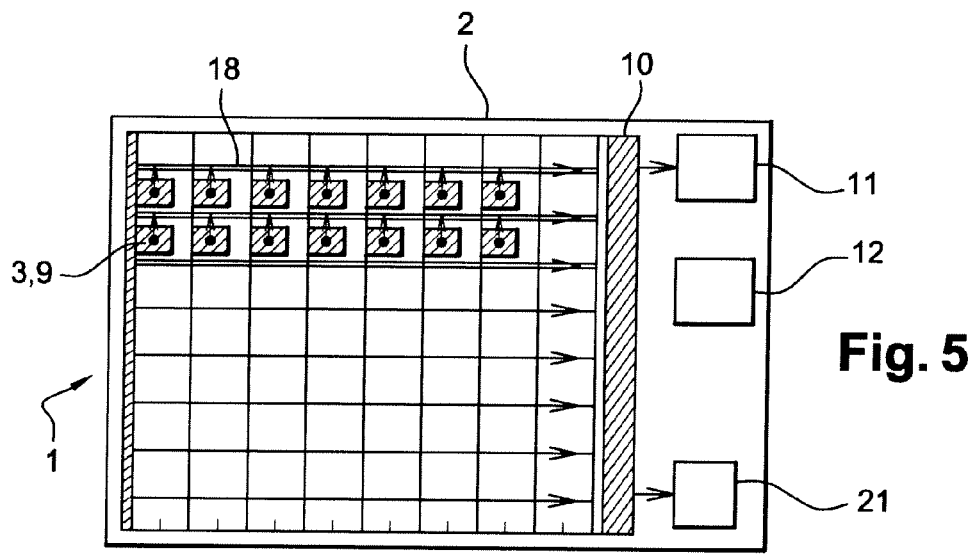
Fig. 5
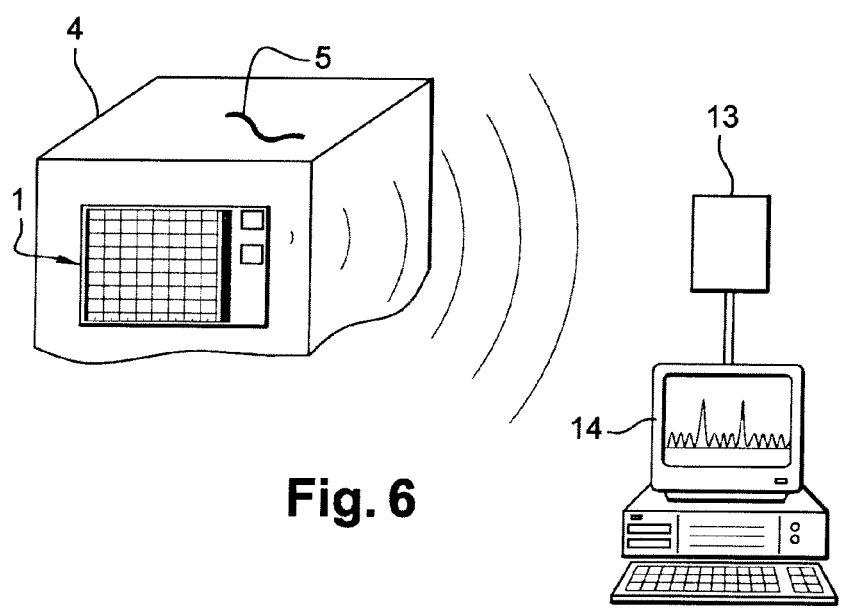
Fig. 6

DEVICE FOR NON-DESTRUCTIVE TESTING OF A COMPONENT BY ANALYZING DISTRIBUTION OF A LEAKAGE MAGNETIC FIELD

CROSS REFERENCE TO RELATED APPLICATIONS

This application is the National Stage of International Application No. PCT/EP2007/054751 International Filing Date, 16 May 2007, which designated the United States of America, and which International Application was published under PCT Article 21 (2) as WO Publication No. WO2007/135051 and which claims priority from French Application No. 0651901, filed on 24 May 2006, the disclosures of which are incorporated herein by reference in their entireties.

This application is also related to U.S. patent application Ser. No. 12/301,702, filed on 20 Nov. 2008, (PAR) (International Application Serial No. PCT/EP2007/054759) and U.S. patent application Ser. No. 12/301,646, filed on 20 Nov. 2008, (PAR) (International Application Serial No. PCT/EP2007/054762) the disclosures of which are incorporated herein by reference in their entireties.

BACKGROUND

1. Field

The disclosed embodiments concern a device for non-destructive control of a component by analyzing distribution of a leakage magnetic field emitted by the component when it is subjected to an exciting magnetic field, comprising means for generating an exciting magnetic field inside the component to be tested, and means for measuring the distribution of the magnetic field emitted by the component in response to the exciting field. The set of means is integrated in a flexible housing to form a device in the form of a flexible coating for being fixed on a region of the surface of the component to be tested. The disclosed embodiments are useful for non-destructive testing (NDT) of aircraft components, but may be used in all industrial sectors where testing the integrity of components is important, such as the automotive, railway, marine, and nuclear industries.

2. Brief Description of Related Developments

In the operation and maintenance of aircraft, it is necessary to employ testing methods that can determine whether the structures have been damaged by cracks or fissures, without harming the parts constituting the structures. The techniques used are jointly referred to as "non-destructive testing" (NDT). NDT techniques are numerous and constantly changing, because the industrial sectors concerned have a need for improved performance from these NDT techniques. The air-transport and civil-engineering sectors are always on the lookout for ever more effective NDT techniques to meet the dual requirements of safety and their desire for cost-reduction.

When dealing with a component made of a non-ferrous metal that is magnetic and conductive, testing techniques are known that are based on Foucault currents. The principle of these techniques resides in using an exciting magnetic field that induces a Foucault current circulation in the component to be tested. The circulation of these induced currents in the component is modified by the presence of defects, fissures, or corrosion. This modification of the distribution of Foucault currents act on the distribution of the magnetic field of the surface of the component generated by the Foucault current. This distribution is generally measured by the induction effect. The information on defects is then extracted from the distribution of the magnetic field.

More recent techniques are also known based on a combination of the exciting magnetic field with a magneto-optical imaging device. The magneto-optical imaging device contains a magnetic material that enables measurement of a generated Faraday rotation that is proportional to the magnetization of the magnetic material in presence of the magneto-optical imaging device from the magnetic field emitted by the component.

All of these means of testing require that the aircraft be immobilized on the ground for the conduct of an inspection of the sensitive areas of the aircraft using the testing apparatus. This entails a relatively long testing period and the presence of a qualified operator, thereby leading to a relatively high maintenance cost.

As far as the designer of this device knows, there is currently no effective means for real time inspecting of the status of structures, e.g., aeronautical structures, throughout their periods of use, and in particular for carrying out an overall evaluation of the health of aeronautical structures while the airplane is in flight.

SUMMARY

The disclosed embodiments propose a device suited to such a real time inspection, which enables the structural health of a structure to be monitored throughout its use by local measurements of the configuration of the leakage magnetic field emitted by said component in response to an exciting field.

The problems faced by such a device are:

to provide a means for non-destructive testing suited for easy connection to the surface of the structures to be tested whether they are accessible or not, while remaining of a negligible mass and size and by requiring only low electric power for its operation, to provide a method for testing adapted to be permanently installed on the components to be tested during their use to perform predictive maintenance by detecting the appearance of defects as soon as possible, thus allowing less expensive repairs to be performed and to guarantee maximum safety of the structures, to provide a means of testing that enables automatic management of the inspections and that provides a full analysis of the structures' health, so as to reduce the operator's work as much as possible in order to reduce the cost of maintenance.

For this purpose, the disclosed embodiments concern a non-destructive testing device of a component in real time. According to the disclosed embodiments, said device contains means for generation of an exciting magnetic field inside the component, said means of generation being incorporated in a housing, said housing being designed to cover the surface of said component to be tested, and means for measuring the distribution of the magnetic field emitted by said component in response to the exciting field, said means of measuring being superimposed on said means for generating the exciting field.

Advantageously the housing is a flexible housing in order to cover the surface of the component taking on the shape of the component.

Advantageously, the means of measurement have a sensitivity suited to determining anomalies in a distribution of the magnetic field likely to reveal the presence of defects in the component.

According to the disclosed embodiments, the means of generation of said exciting magnetic field contains a network of micro-spools, each of said micro-spools have alternating current flowing through them in order to generate said exciting magnetic field.

In another embodiment, the means for generation of said exciting magnetic field contains a network of micro-magnets.

In one embodiment said means of measurement include a liquid crystal membrane sensitive to the magnetic field and a network of opto-electronic microsensors superimposed on said liquid crystal membrane. Each opto-electronic microsensor includes a photosensitive cell to transform light radiation received in the form of electric signals, said cell being coupled to a charge transfer device to collect electric signals.

In another embodiment said means of measurement contain a network of magnetoresistive microsensors in order to directly measure said distribution of the magnetic field emitted by said component.

According to a particular embodiment, said networks are organized in a matrix of lines and columns.

In addition, the device contains an interface electronics assembly connecting said means of measurement to a recording memory. The electronics interface and the memory are incorporated into the flexible housing (2) so as to advantageously provide a monolithic testing device.

The testing device advantageously contains a calculating system such as a microprocessor to automatically identify the information relative to defects such as the size, location, and nature of the defects from the distribution of the magnetic field emitted by the component to be tested.

According to one embodiment of the device, said calculating system is not incorporated into the flexible housing, said testing device contains a means of transmitting, to send the electrical signals recorded in the recording memory to said calculating system by using a radio or infrared wired or wireless link.

In another embodiment said calculating system is incorporated into the said flexible housing and is connected between said interface electronics and said recording memory.

According to the disclosed embodiments, the calculating system includes a memory containing at least one reference map of the magnetic field of the component(s), a means of calculation for converting the electrical signal received by said calculating system in a representative signal of the distribution of the leakage magnetic field measured by the microsensors, and means for analysis of said distribution of the magnetic field by comparison with the reference distribution of the magnetic field.

The means for analysis includes the means for comparative analysis between the measured distribution of the magnetic field and the reference distribution of the magnetic field. Advantageously, said means for comparative analysis includes means to generate a status signal S and information relative to the defects present in the component.

Advantageously, said status signal S and said information are being transmitted either by said calculating system to a means of alarm or recorded in said recording memory linked to said calculating system, then sent to the means of alarm by using a radio or infrared wired or wireless link.

The means of alarm may preferably contain a display means and light or sound indicators.

Other characteristics and advantages of the disclosed embodiments will be better understood by reading the following description and referring to the drawings, which show:

BRIEF DESCRIPTION OF THE DRAWINGS

In FIGS. 4.A and 4.B: Two schematic diagrams illustrating respectively the operational principle of a GMR (giant magnetoresistive effect) cell in a null field and under magnetic field;

In FIG. 5: a schematic diagram of a top view of a testing device, showing an embodiment of the device;

In FIG. 6: a schematic diagram of the testing device from FIG. 5 in operating position for transmitting the electrical signal to a remote calculating system, In FIG. 7: a schematic diagram of a network of testing devices arranged on the surface of the components of an airplane on the ground, in position to transmit the signals recorded while the plane was in flight.

When a component is submitted to significant mechanical stresses, sometimes in a cyclical manner, after a certain amount of time, fatigue cracks will appear in the component. When the component is submitted to an exciting magnetic field, the presence of these fissures constitutes magnetic barriers and act on the distribution of the magnetic field emitted by the component in response to an exciting magnetic field. By establishing a map of this distribution of the magnetic field emitted by the component and by implementing suitable means of analysis, the information relative to the defects present in the component may be extracted from the map of the distribution of the magnetic field.

In the case of a non-ferrous metal that is magnetic and conductive, the exciting magnetic field induces the circulation of a Foucault current in the component. The Foucault currents that appear inside the component generate a radiant leakage magnetic field in their circuit around the component. The characteristics of these currents are narrowly linked to the characteristics of the components such as their form, their conductivity. These currents may be modified by the existence of structural defects, fissures or corrosion. The modification of these distributions of Foucault current act then on the distribution of the magnetic field emitted by the component to be tested. By precisely establishing a map of the distribution of the magnetic field emitted by the component, defects and fissures may be located.

In the case of a ferromagnetic component that presents a structure in different magnetic directional fields, the exciting magnetic field directly reorients the magnetization of each field and consequently modifies the magnetic field configuration of the component. The new magnetic field configuration is then disrupted by the possible presence of the defects, fissures or corrosion. By establishing a magnetic map of the ferromagnetic components, defects and fissures may be located.

DETAILED DESCRIPTION OF THE DISCLOSED EMBODIMENTS

Figure 1:
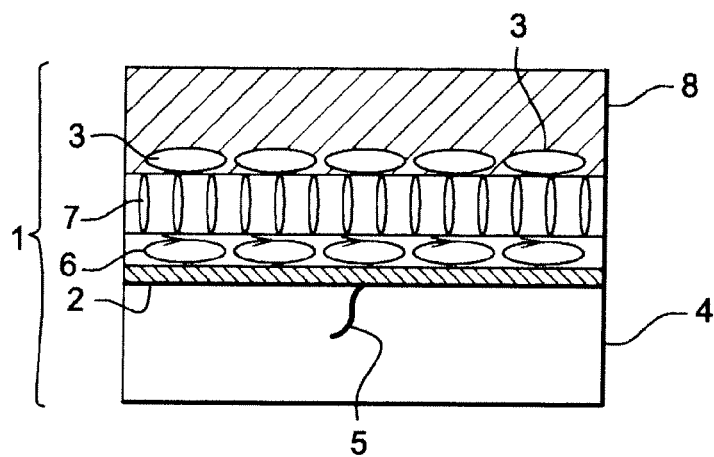
In FIG. 1: a schematic side view of a section according to one embodiment containing a network of micro-spools to generate an exciting magnetic field, a liquid crystal membrane and an opto-electronic microsensor network, the device covering the surface of the component to be tested and being covered by a layer of paint.
Figure 3:
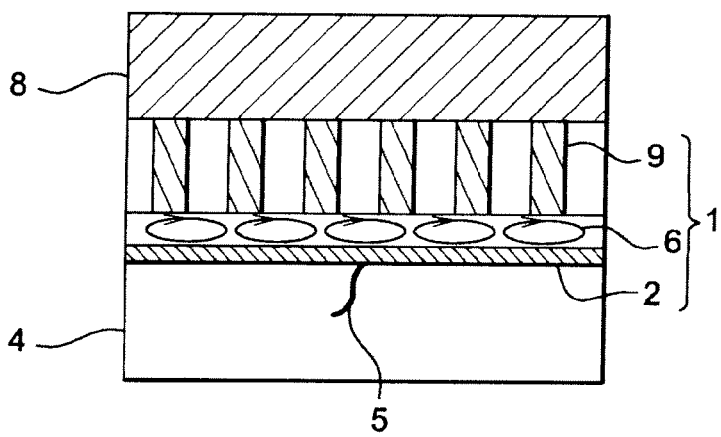
In FIG. 3: a schematic diagram of a side view of a section of a testing device according to another embodiment containing a network of micro-spools, a network of magnetic microsensors based on magnetic resistance, said device covering the surface of a component to be tested and being itself covered by a coat of paint.

In FIGS. 1 and 3, two embodiments are shown of the non-destructive testing device of a component by analyzing the distribution of the magnetic field. It contains the means for generating an exciting magnetic field inside the component and means of measurement suitable for determining a distribution of the leaking magnetic field emitted by the component, the means of measurement being superimposed on the means of generation. The means of generation is integrated in a housing (2) that will attach to an area of the surface of the component to be tested.

Advantageously, this housing (2) is a flexible housing that is for example made of a plastic material enabling the testing device (1) to be attached to the surface of the component to be tested, by following the shape of the component. This connection is carried out via an adhesive material. Preferably, the adhesive material chosen makes it possible to remove the device from the component to be tested, so as to be able to easily change the device when it is damaged.

This device should preferably be produced in a limited adjustable size to be attached to a critical area of the component where cracks are liable to appear. On an aircraft, the device may be placed on areas regarded as critical, located for example where the elements are attached, at the level of the assembly elements of the panels, and in areas where there is a strong concentration of stress.

Advantageously, this testing device is designed to receive a surface coating (8), which may for example be a coat of paint that covers the testing device.

Figure 2:
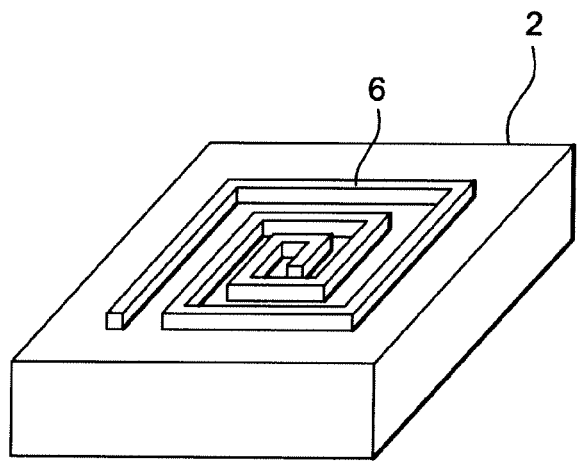
In FIG. 2: A schematic diagram of a top view of a microspool according to one embodiment.

One non-limiting example, of an embodiment of the means of generation of the magnetic field is described in relation to FIG. 1 and FIG. 2. In this example, the means of generation of the exciting magnetic field contains a network of micro-spools (6) suited to generating an exciting magnetic field being able to penetrate into the inside of a component (4) to be tested.

In another example of the embodiment of the means for generating said exciting magnetic field contains a network of micro-magnets the magnetization of which is maintained by electronics located on the periphery (10) of the housing.

Advantageously, the means of generating the magnetic field is decoupled with the means of measurement, in which case, the means of generating the magnetic field includes a single macro-spool suited for generating a magnetic field able to penetrate into the component (4).

In one particular embodiment, the network of micro-spools is organized in a matrix of lines and columns. Each micro-spool has alternating current running through it. For example, the micro-spools may be created by a procedure of microlithography including one photolithography stage in order to obtain a resin mold of the micro-spools and a second stage of electrolytic deposit of a metal, which may be for example, copper. The resin is then removed by a solvent. Within the framework of the disclosed embodiments, the substrate upon which the micro-spools are created is a flexible substrate made of a plastic material so as to take on the form of the surface of the component upon which is placed the testing device (1) in order to respond to the need for components of different shapes.

FIG. 2 describes a specific example of one form of micro-spool (6) constituted by rolling three rectangular, flat spirals. The measurements of each spiral are around ten micron and the size of the of the micro-spool is around 100 micron. The measurements of each spiral are adapted in order to concentrate the current in the spiral, while having a sectional copper surface that enables an effective connection to the substrate and thermal dissipation. The local magnetic field obtained by these micro-spools is suitable for penetrating into the component to be tested.

In FIG. 1, an embodiment is shown of the means of measurement for a distribution of magnetic field generated by the Foucault currents created inside the component to be tested directly by the magnetic fields of the ferro-magnetic component to be tested including a liquid crystal membrane (7) superimposed on the micro-spools network (6). The liquid crystals are sensitive to the magnetic field and ready to be directed according to the intensity and the direction of the field. For example, the liquid crystal membrane is trapped between two plastic housings. The structure of these liquid crystals is modified according to the direction and intensity of the leakage magnetic field by the Foucault current inside the component; this is translated by a variation of the spectral composition of the reflected waves by the various planes of the liquid crystals, consequently leading to a change in color on the surface of the liquid crystal membrane (7). The distribution of the magnetic field emitted from the component is thus restored by the liquid crystal membrane under the form of a light spectrum selectively sent by said planes of the liquid crystals.

To detect this change in color according to the magnetic field, a network of opto-electronic microsensors (3) is superimposed on this liquid crystal membrane (7). Each opto-electronic microsensor is capable of transforming the luminous radiation emitted by the liquid crystal membrane into electronic charges through a photosensitive cell that converts light energy into electric charges. Each cell is coupled to a charge transfer device that has for its function to evacuate the electrical charge. An electrical signal representative of the luminous energy received by the photosensitive cell is thus generated by the charge.

Preferably, the incident light waves on the surface of the membrane come from a light source integrated into each opto-electronic microsensor (3).

In another embodiment, the means of measurement of the distribution of the magnetic field include only a microsensor network which play a role of detector at the same time assuring in this way the role of the liquid crystal membrane, of emitter and of receptor. The microsensors are capable of storing information representative of the distribution of the magnetic field and is capable upon command of sending or of automatically sending following a cyclical request when information indicates that values are higher than the threshold.

In FIG. 3 another embodiment of means of measurement is shown including a magnetoresistive microsensor network (9) to directly measure the distribution of the magnetic field generated either by the Foucault currents or by the magnetic fields of the component to be tested. The operational principle of the magnetoresistive microsensors is based on the variation of electrical resistance of a magnetic material according to the direction applied to the magnetic field. The magnetoresistive microsensors are preferably GMR effect (giant magnetoresistive effect) microsensors presenting a significant variation of electrical resistance in comparison to the electrical resistance of a null field. Generally this electrical variation is around 16%.

In the specific embodiment of GMR effect microsensors, each GMR effect microsensor is constituted by a Wheatstone bridge of four GMR magnetoresistances. When the bridge is in equilibrium, the output voltage on the bridge is null. Under the action of a non-uniform magnetic field, the bridge becomes out of equilibrium, and an output voltage proportional to the variation of the magnetic field appears. FIGS. 4.A and 4.B respectively describe a magnetoresistance including a stack of ferromagnetic layers (16) and non-magnetic layers (17) the thickness of which is of a few nanometers respectively in the null field, and in presence of an applied magnetic field. In the null field, the magnetization represented by the arrows on the ferro-magnetic layers (16) on both sides of the non-ferro-magnetic layer (17) are oriented in opposite directions. It is difficult for electrons to pass perpendicularly through the layers, thus inducing an elevated resistance $R_{10}$. Under the action of the applied magnetic field, the magnetizations are oriented parallel to the applied field; this configuration allows electrons to pass more easily, inducing in this way a reduction in the resistance $R_1$.

Magnetoresistances are created, for example, by a microlithographic process in a stack of ferromagnetic or non-magnetic layers including a photolithographic stage of engraving to obtain a network of magnetoresistive pillars.

FIG. 5 is a schematic diagram of a top view of the test device according to the embodiments presented previously. According to one specific embodiment the device has a rectangular form including here, as an illustration, a network of 56 opto-electronic (3) or magneto-resistive (9) microsensors organized in a matrix of lines and columns.

The testing device also contains an interface electronics (10) connecting the microsensor network (3, 9) to a recording memory (11). The electronics (10) and the memory (11) are also incorporated into the flexible housing (2) so as to advantageously provide a monolithic testing device.

The data in the form of electrical charges characteristic of the local magnetic field measured by the microsensors (3, 9) are transmitted to the electronic interface assembly (10) that includes an amplifier, for example, to increase the power of the signal in order to improve the Signal to Noise Ratio and also a digital/analog converter to convert the analog electric signals received into digital signals. The electric signal that exits the interface electronics may be an intensity, or a voltage.

The amplified electric signal is then routed to the recording memory (11). The interface electronics (10) are placed at the end of the microsensor lines in the shown in FIG. 5. In another embodiment, the electronics of the interface (10) might be placed at the end of the microsensor columns.

The organization of the microsensors in the matrix of lines and columns enables obtaining a map of the distribution of the magnetic field of the type that a defect in the component may be located on the surface of the component.

In order to locate the defects precisely, the spacing between microsensors is preferably set at a value lower than the minimum size of the defects to be detected, such that the position of the defects can be determined, and such that in the event of local damage to the microsensor network the microsensors located around the damaged area will always allow monitoring of the areas closest to a possible equipment defect in the monitored area.

In one specific embodiment, the mode of transfer of the electrical signal coming from the microsensors (3, 9) to the interface electronics (10) is an interlinear transfer mode. Above each line of microsensors there is a storage line 18. The signal is temporarily stored in this storage line (18).

The content of the storage lines is then transferred to the interface electronics (10) in parallel mode. The electronic signals are then removed in series to a recording memory (11).

In a variant of the electric-signal transfer mode, each microsensor is addressed directly to send its electric signal directly to the interface electronics (10).

In order to automatically process the electric signal measured by the microsensors, the testing device also includes a calculating system (13) to convert the electric signal into a electric signal representative of the leakage magnetic field emitted by the component and to determine a distribution of the magnetic field. The calculating system may be a microprocessor system.

In a preferred embodiment, shown in FIG. 6, since the calculating system is not incorporated into the flexible housing (2), the device contains a means of transmission, (12) to send the electrical signal recorded in the recording memory (11) to the calculating system (13) by using a wireless radio or infrared link. This means of transmission contains for example a transponder integrated into the flexible support, which preferably operates on a fixed frequency, said frequency being chosen so that the transmission of the electrical signal representative of the distribution of the leakage magnetic field on the component does not interfere with the transmission of other data by devices other than the testing device (1).

The transmission means (12) for sending the recorded electric signals in the memory (11) to the calculating system (13) may also be a wired link.

The electric signal received by the calculating system (13) is converted into a signal representative of the leakage magnetic field of the component due to the calculation means in which is integrated an adapted theoretical model linking the magnetic field to the electric charge.

These means of calculating generating the mapping that may be an amplitude map, and a spectral representation of the magnetic field. This data representing the distribution of the magnetic fields emitted by the component is then sent to the analysis means.

The means for analysis includes means for comparative analysis to perform a comparative amplitude study between the distribution of the magnetic field measured by the microsensor network and the reference distribution. Advantageously, this means of comparative analysis enables the establishment of a field map of a variation distribution of the leakage magnetic field of the component. For this purpose the calculating system contains a memory in which a database of distribution maps of the reference magnetic field of the component is recorded. These reference mappings constitute a predefined model for comparison with the behavior of the area covered by the testing device. This reference mapping can be predetermined on a reference component. "Reference component" means a component considered not to contain any defect, e.g., a component leaving the end of its production line, having successfully completed all the qualification stages. They may also be predetermined by modeling. In this embodiment, the calculating system is preferably a portable system. When the means of analysis performs an amplitude comparison between the reference magnetic field and the distribution of the magnetic field measured by the microsensors, if the calculated differential value between the reference field and the measured field exceeds a threshold value, a status signal S is generated by the means of analysis.

Advantageously, the means for analysis includes means for spectral analysis that determines a spectral representation of the leakage magnetic field measured by the microsensors for determining the information relative to the defects present in the component. Specifically, the spectral analysis enables determination of the nature of the defects and their size.

Within the framework of real-time testing of the structures, the testing device may for example be programmed to be activated while the aircraft is no longer on the ground and it then performs measurements at regular intervals, e.g., every 5 minutes over a predetermined period so as to perform time-based measurements. In this way the testing device enables a mapping of the area monitored over time, to establish the development of the distribution of the magnetic field.

The status signals as well as all information such as the nature of the defects, the size of the defects, and the locations of the defects are transmitted by the calculation system to the means of alarm (14) which may include a display panel (22) to display the information and light and/or sound indicators (20) to warn the maintenance operator.

The transmission of electrical signals recorded in the memory (12) to the calculating system can be programmed so that it is carried out automatically, for example at the end of an aircraft's flight. This transmission can also be activated manually by the maintenance operator, by querying the testing device during inspection of the plane.

In another embodiment, the calculating system (13) is directly incorporated into the flexible housing (2) and connected between the interface electronics (10) and the recording memory (11). In this embodiment, the calculating system (13) receives the electrical signals directly from the interface electronics (10) and sends only the status signal and information on defects to the recording memory (12). During an inspection, by querying the device, the operator downloads the status signals and the information recorded in the testing device's memory to the means of alarm (14) by using a radio or infrared wired or wireless link.

Figure 7:
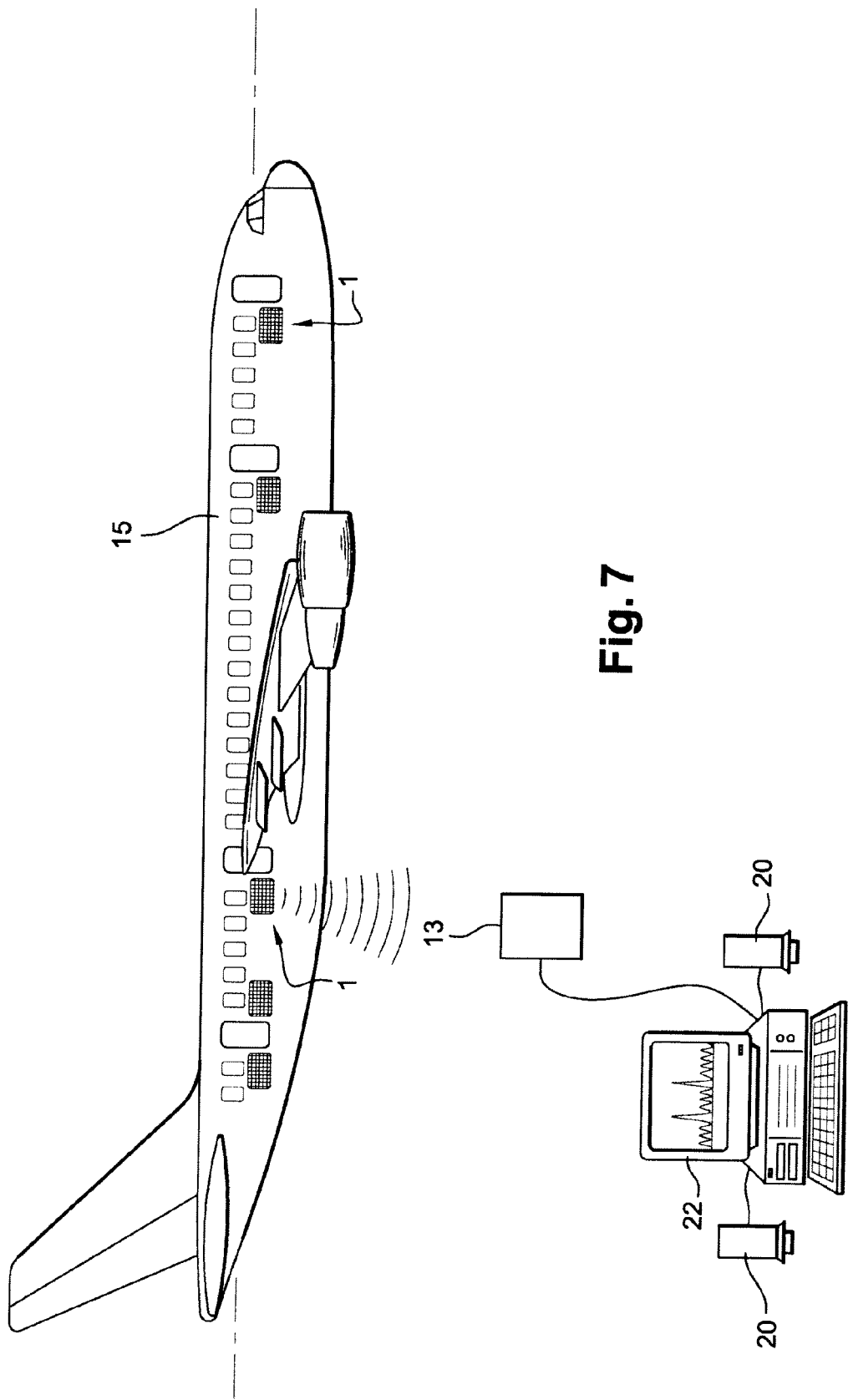

FIG. 7 is a schematic view of a network of testing devices (1) arranged on the surface of the structures of an aircraft (15). The airplane is on the ground and the network of testing devices (1) is in the position for transmitting the signals recorded during one or more flights by the aircraft to a calculating system (13), which is connected to a means of alarm (14); here, these include a computer with a monitor (22) and sound indicators (20).

All the electronic components incorporated in the flexible housing are produced by a micro-manufacturing technology on a hard substrate, transposed here on a flexible substrate such as a plastic substrate. However, the temperature used during the course of micro-manufacturing process is likely to destroy the plastic substrate. One of the solutions currently proposed consists of producing the components first on a hard substrate, itself deposited on glass. The hard substrate may be, for example, made of silicon, of aluminum, $Al_2O_3$. Another layer of glass to serve as protection is then fixed onto the components with a soluble adhesive, and the hard substrate is then removed from the stack by ablation with a laser. The components are applied to a plastic substrate and fixed to it with a permanent adhesive, and the protective glass is removed.

In one specific embodiment, the testing device is presented in the form of a thin film having a thickness of around 50 μm, and a surface of 10×10 cm sideways that integrates the microsensor with a size of about one hundred micron, with a step of around ten micron.

The disclosed embodiments were presented within the framework of testing aircraft components, but may be used in any industrial sector where testing the integrity of workpieces is important, such as the automotive, railroad, naval-construction, or nuclear sectors.

The invention claimed is:

1. A non-destructive testing device for testing an electrically conductive component comprising:
    means to generate an exciting magnetic field, wherein said means of generation is incorporated in a housing suitable for covering an area on a surface of said component to be tested, and
    means of measuring, different from the means of generation, for measuring a distribution of a magnetic field emitted by said component to be tested subjected to said exciting magnetic field when said housing is on the area on the surface of the component, wherein said means of measuring the distribution of the magnetic field is superimposed on said means of generation,
    wherein said means of measuring includes a liquid crystal membrane sensitive to the magnetic field emitted by said component to be tested and a network of opto-electronic microsensors superimposed on said liquid crystal membrane.

2. A device according to claim 1, wherein said housing is a flexible housing covering the area on the surface of the component while taking on a shape of the component.

3. A device according to claim 1, wherein said means of measurement includes an assembly of microsensors suitable for generating a map of the distribution of the magnetic field on the surface of said component.

4. A device according to claim 3, wherein dimensions and layout of the microsensors are determined to detect variations in the distribution of the magnetic field caused by a presence of a defect.

5. A device according to claim 1, wherein said means of generation of said exciting magnetic field comprises a network of micro-spools, each of said micro-spools conducting alternating current to generate said exciting magnetic field.

6. A device according to claim 1, wherein said means for generation of said exciting magnetic field comprises a network of micro-magnets.

7. A device according to claim 1, wherein each opto-electronic microsensor includes a photosensitive cell to transform light radiation received in a form of electric charges, said cell being coupled to a charge transfer device to collect electric signals.

8. A device according to claim 1, wherein said network is organized in a matrix of lines and columns.

9. A device according to claim 8, comprising interface electronics connecting said means of measurement to a recording memory.

10. A device according to claim 9, wherein said interface electronics and said recording memory are incorporated into said flexible housing so as to form a monolithic testing device.

11. A device according to claim 9, wherein said interface electronics are placed at an end of the opto-electronic microsensor lines.

12. A device according to claim 9, wherein said interface electronics are placed at an end of the opto-electronic microsensor columns.

13. A device according to claim 9, comprising a calculation system.

14. A device according to claim 13, comprising means of transmission for sending electrical signals recorded in the recording memory to said calculating system by using a radio or infrared wired or wireless link.

15. A device according to claim 13, wherein said calculating system is incorporated into said flexible housing and is connected between said interface electronics and said recording memory.

16. A device according to claim 13, wherein the calculating system comprises:
    a memory comprising at least one reference map of a reference distribution of a magnetic field of the component,
    a means of calculation for converting electrical signals representing the distribution of the emitted magnetic field, and
    a means for analysis of said distribution of the emitted magnetic field in comparison with the reference distribution of the magnetic field.

17. A testing device according to claim 16, wherein at least one map of the reference distribution of the magnetic field is predetermined from a reference component.

18. A testing device according to claim 16, wherein at least one map of the reference distribution of the magnetic field is predetermined by modeling.

19. A testing device according to claim 16, wherein said means of analysis includes a means of analysis to compare the measured distribution of the magnetic field and the reference distribution of the magnetic field.

20. A device according to claim 19, wherein said means for comparative analysis includes means to generate a status signal S and information relative to defects present in the component.

21. A device according to claim 20, wherein said status signal S and said information are transmitted by said calculation system to an alarm means.

22. A testing device according to claim 21, wherein said status signal S and said information are recorded in said recording memory connected to said calculation system, then transmitted to the alarm means by the radio or infrared wired or wireless link.

23. A testing device according to claim 21, wherein said alarm means includes a means of display and light or sound indicators.

24. A testing device according to claim 1, wherein said opto-electronic microsensors are about one hundred micron in size.

25. A testing device according to claim 1, wherein a thickness of said testing device is lower than or equal to 50 μm.

26. A testing device according to claim 1, wherein said flexible housing of the testing device is fixed to the surface of the component to be tested, by means of an adhesive material.

* * * * *